United States Patent [19]

Warriner

[11] Plant 5,120

[45] Oct. 11, 1983

[54] ROSE PLANT 72-12551

[75] Inventor: William A. Warriner, Tustin, Calif.

[73] Assignee: Jackson & Perkins Company, Medford, Oreg.

[21] Appl. No.: 353,523

[22] Filed: Mar. 1, 1982

[51] Int. Cl.[3] ..... A01H 5/00

[52] U.S. Cl. ..... Plt./20

[58] Field of Search ..... Plt./20

*Primary Examiner*—Robert E. Bagwill

*Attorney, Agent, or Firm*—Klarquist, Sparkman, Campbell, Leigh, Whinston & Dellett

[57] ABSTRACT

A hybrid tea rose variety having a well branched, upright plant bearing many flowers; uniform orange-red flower color; stiff petals; little fragrance.

1 Drawing Figure

This present invention relates to a new and distinct variety of rose plant of the hybrid tea class which was originated by me by crossing the variety Merci with the pollen of an unnamed variety, which itself was a cross between the variety Bridal Pink and the variety Tiffany.

The primary objective of this breeding was to produce a new rose variety combining the abundance of bloom of Merci with the larger orange blooms of the pollen parent. This objective was substantially achieved along with other desirable improvements as evidenced by the following unique combination of characteristics which are outstanding in the new variety and which distinguish it from its parents, as well as from all other varieties of which I am aware:

1. An upright plant, well branched, bearing large numbers of flowers.
2. A uniform flower color of an orange-red, RHS 34B.
3. Stiff petals, holding good flower form until petals drop.
4. Very little fragrance.
5. Normal amount of large prickles and more than average small prickles.

Asexual reproduction of this new variety by budding, as performed at Wasco, Calif., shows that the foregoing characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color in terminology in accordance with The Royal Horticultural Society Colour Chart except where ordinary dictionary significance of color is indicated.

Parentage:

*Seed parent.*—Merci.

*Pollen parent.*—Unnamed (Bridal Pink × Tiffany).

Classification:

*Botanical.*—Rosa hybrid.

*Commercial.*—Hybrid tea.

FLOWER

Observations made from specimens grown at Irvine, Calif. during October.

Blooming habit: Continuous.

Bud:

*Size.*—1 inch when petals start to unfurl.

*Form.*—Short, blunt top.

*Color.*—When sepals first divide, Red 43B to 43C; when half blown, upper side of petals Red 42B aging quickly upon exposure to Red 42A; lower side of petals near Red 37B.

*Sepals.*—Color: Outer surface Green 138A with numerous stipitate glands on surface. Three appendaged sepals lightly appendaged; two unappendaged sepals hairy edged.

*Receptacle.*—Color: Green 138B. Shape: Funnel. Size: Large, long. Surface: Smooth.

*Peduncle.*—Length: Short. Surface: Very lightly glandular and hairy. Color: Light green. Strength: Stiff, erect.

*Opening.*—Petals fold out.

Bloom:

*Size.*—Medium. Average open size 3½ to 4 inches.

*Borne.*—Singly or several together.

*Stem.*—Long, strong.

*Form.*—When first open, high center. Permanence: Outer petal edges slightly curled.

*Petalage.*—Number of petals under normal conditions: 40–45.

*Color.*—Center of flower: upper side of petals Orange-Red 34B; reverse side of petals Orange-Red 34C; base of petals slightly yellow surrounded by white, white only on reverse side. General tonality from a distance, Orange-Red 34A, 34B.

*Variegations.*—Occasional streak of lighter color in one or more petals.

*Discoloration.*—General tonality at end of first day, aging to darker Orange-Red 34A on tips of petals; third day, ages to Red 42A.

*Fragrance.*—Slight.

Petals:

*Texture.*—Thick.

*Shape.*—Deltoid.

*Form.*—Tips slightly recurved.

*Arrangement.*—Imbricated. Petaloids in center: few.

*Persistence.*—Drop off cleanly.

*Lastingness.*—On the plant, long. As cut flower, long.

Reproductive parts:

*Anthers.*—Medium. Color: Yellow. Arrangement: Regular around styles.
*Filaments.*—Color: Pink.
*Pollen.*—Lemon yellow.
*Styles.*—Color: Reddish purple.
*Stigmas.*—Color: Yellow.

PLANT

Form: Bush.
Growth: Vigorous, upright.
Foliage: Number of leaflets on normal mid-stem leaves: 5 or 7.
*Size.*—Medium.
*Quantity.*—Normal.
*Color.*—New foliage: Greyed Purple 183A. Old foliage: Green 137A.
Leaflets:
*Shape.*—Oval.
*Texture.*—Upper side: Leathery.
*Edge.*—Serrated.
*Serration.*—Single, small.
*Petiole.*—Rachis: Color: Green. Underside: Prickles.
*Stipules.*—Long, bearded.

*Disease resistance.*—Partly resistant to mildew under normal growing conditions at Irvine, Calif.
Wood:
*New wood.*—Color: Light green. Bark: Smooth.
*Old wood.*—Color: Green. Bark: Smooth.
Prickles:
*Quantity.*—On main stalks from base, ordinary. On laterals from stalk, ordinary.
*Form.*—Long, hooked downward.
*Color when young.*—Brown.
*Position.*—Irregular.
Small prickles:
*Quantity.*—On main stalks, many. On laterals, many.
*Color.*—Brown.

I claim:

1. A new and distinct variety of rose plant of the hybrid tea class, substantially as herein shown and described, characterized particularly as to novelty by the unique combination of its upright plant, orange-red flowers of little fragrance and excellent form and substance and numerous small prickles on the canes.

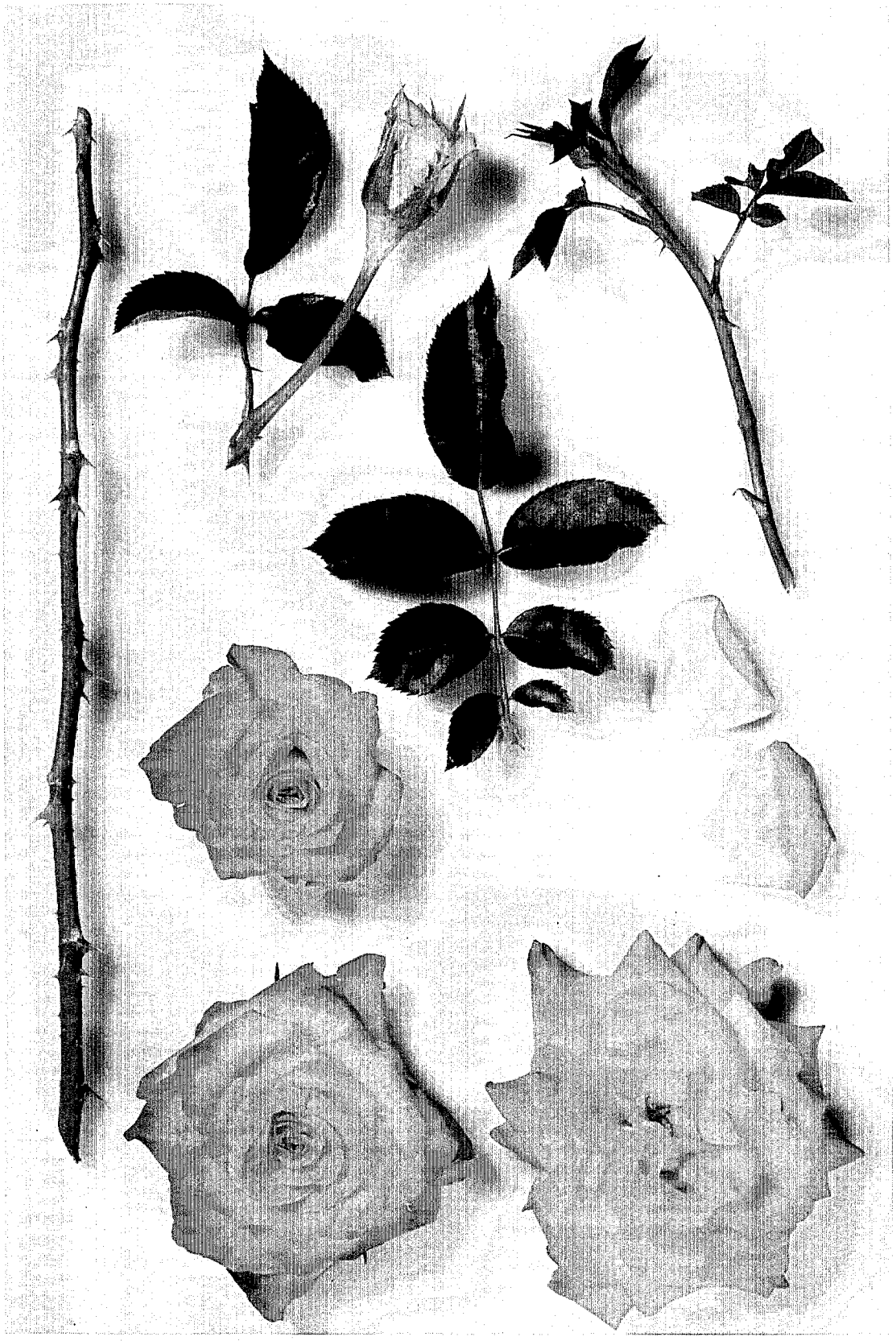

* * * * *